(12) United States Patent
Eibl

(10) Patent No.: US 8,741,846 B2
(45) Date of Patent: Jun. 3, 2014

(54) STORAGE-STABLE, FUNCTIONALLY INTACT FIBRINOGEN

(75) Inventor: Johann Eibl, Vienna (AT)

(73) Assignee: Bio-Products & Bio-Engineering AG, Vienna (AT)

( * ) Notice: Subject to any disclaimer, the term of this patent is extended or adjusted under 35 U.S.C. 154(b) by 413 days.

(21) Appl. No.: 13/000,934

(22) PCT Filed: Jun. 22, 2009

(86) PCT No.: PCT/AT2009/000248
§ 371 (c)(1),
(2), (4) Date: Jan. 13, 2011

(87) PCT Pub. No.: WO2009/155626
PCT Pub. Date: Dec. 30, 2009

(65) Prior Publication Data
US 2011/0114524 A1    May 19, 2011

Related U.S. Application Data

(60) Provisional application No. 61/074,830, filed on Jun. 23, 2008.

(51) Int. Cl.
| A61K 38/00 | (2006.01) |
| A61P 7/08  | (2006.01) |
| A61B 17/06 | (2006.01) |
| A61B 19/02 | (2006.01) |
| A61L 15/00 | (2006.01) |
| A61K 9/00  | (2006.01) |

(52) U.S. Cl.
USPC ............................ 514/15.3; 206/438; 424/400

(58) Field of Classification Search
None
See application file for complete search history.

(56) References Cited

U.S. PATENT DOCUMENTS

| 6,277,961 | B1  | 8/2001 | Hock et al. |
| 6,447,774 | B1  | 9/2002 | Metzner et al. |
| 7,045,601 | B2 * | 5/2006 | Metzner et al. ............... 530/382 |
| 2006/0009376 | A1 * | 1/2006 | Eibl .................................. 514/2 |

FOREIGN PATENT DOCUMENTS

| AU | 2006202680 | 1/2007 |
| DE | 68922358 | 10/1995 |
| DE | 69303941 | 3/1997 |
| DE | 19853033 | 5/2000 |
| DE | 10261126 | 3/2004 |
| EP | 0345246 | 12/1989 |
| EP | 1393741 | 3/2004 |
| EP | 1568709 | 8/2005 |
| WO | 91/19519 | 12/1991 |
| WO | 97/26280 | 7/1997 |
| WO | 00/71153 | 11/2000 |
| WO | 2004/054607 | 7/2004 |

OTHER PUBLICATIONS

Frederick H. Silver, et al "Review: Preparation and use of fibrin glue in surgery" Biomaterials, vol. 16, No. 2 (1995) pp. 891-903.
Kathleen E. Brummel, et al "An Integrated Study of Fibrinogen during Blood Coagulation" The Journal of Biological Chemistry, vol. 274, No. 32, Issue of Aug. 6, 1999, pp. 22862-22870.
David A. Meh, et al "Identification and Characterization of the Thrombin Binding Sites on Fibrin" The Journal of Biological Chemistry, vol. 271, No. 38, Issue of Sep. 20, 1996, pp. 23121-23125.
Victor J. Marder, et al "High Molecular Weight Derivatives of Human Fibronogen Produced by Plasmin" The Journal of Biological Chemistry, vol. 244, No. 8, Issue of Apr. 25, 1969, pp. 2111-2119.
M. Mosesson "Antithrombin I. Inhibition of thrombin generation in plasma by fibrin formation" Thromb Haemost 2003;89:9-12.
John R. Shainoff, et al "Fibrin precursors, intermediaries for hemostasis in the clot war" Thrombosis Research, vol. 105, Issue 1, Jan. 1, 2002, pp. 3-13.
Birger Blombaeck "Fibrinogen and Fibrin-Proteins With Complex Roles in Hemostasis and Thrombosis" Thrombosis Research, vol. 83, Issue 1, Jul. 1, 1996, pp. 1-75.

* cited by examiner

*Primary Examiner* — Marcela M Cordero Garcia
(74) *Attorney, Agent, or Firm* — Workman Nydegger

(57) ABSTRACT

Method for the production of a fibrinogen solution from an aqueous solution that contains functionally intact fibrinogen and is contaminated with profibrin and/or fibrin monomers and/or fibrin monomer complexes and/or fibrin split products, characterized in that the contaminations are precipitated using a non-denaturing precipitating agent at a temperature ranging from −4° to +4° and calcium ion activity not exceeding that of a 1,000 μM $CaCl_2$ solution and are separated from the solution by means of filtering or centrifugation process.

14 Claims, No Drawings

STORAGE-STABLE, FUNCTIONALLY INTACT FIBRINOGEN

The invention relates to a storage-stable, functionally intact fibrinogen, a fibrinogen concentrate and a medicinal product that contains fibrinogen. The invention further relates to a method for producing a fibrinogen solution by separating impurities from an aqueous solution that contains functionally intact fibrinogen.

Injuries of blood vessels result in more or less severe bleedings, which are controlled by coagulation of the blood in the injured vessels. However, blood may also coagulate in non-injured vessels by other vessel damage, and the resulting thrombi may interrupt the blood circulation locally. Responsible for blood coagulation are thrombin, which transfers the soluble fibrinogen into insoluble fibrin, as well as activated platelets. (Brummel K E et al: An Integrated Study of Fibrinogen during Blood Coagulation. J B Chem 1999; 274(32): 22862-22870. Blombäck B: Fibrinogen and Fibrin-Proteins with Complex Roles in Hemostasis and Thrombosis. Thromb Res 1996; 83(1):1-75).

Thrombin splits fibropeptides A and B enzymatically from intact fibrinogen, soluble fibrin monomers resulting in that process. These soluble fibrin monomers aggregate into still soluble fibrin monomer complexes, which further aggregate into insoluble fibrin. Low quantities of thrombin can split off only one of the two fibropeptides A contained in the fibrin molecule, which results in the formation of α-profibrin (Shainoff J R et al: Fibrin precursors, intermediaries for hemostasis in the clot war. Thromb Res 2002; 105:3-13).

For the enzymatic effect of thrombin on fibrinogen, which causes the splitting off of fibrinopeptide A and subsequently to the splitting off of fibrinopeptide B, thrombin needs to bind to the splitting sites of the fibrinopeptides in the fibrinogen molecule. Beyond that, thrombin is bound to the fibrinogen molecule at two more sites where it cannot cause splitting. The thrombin thus bound is enzymatically ineffective and, because of its binding, is not available for other enzymatic reactions. The property of fibrinogens to bind thrombin also at sites in the molecule where it cannot exert enzymatic activity is known as antithrombin I activity (Mosesson M: Antithrombin I Inhibition of thrombin generation in plasma by fibrin formation. Thromb Haemost 2003; 89:9-12. Meh D A: Identification and Characterization of the Thrombin Binding Sites on Fibrin. J B Chem 1996; 271(38):23121-23125).

Fibrinogen concentrates for pharmaceutical purposes are used for both, topical application to achieve hemostasis and tissue sealing, and for intravenous infusions to treat a-, hypo- and dysfibrinogenemia and consumption coagulopathy. Such medicinal products are available in deep-frozen or freeze-dried form and are storable for 18 to 36 months. Either form has disadvantages. Deep-frozen fibrinogen solutions need to be stored and transported deep-frozen, and the subsequent thawing process takes time. Although freeze-dried fibrinogen concentrates can be stored at refrigerator temperature, the required long reconstitution time prevents their prompt application. Both, the thawed and the reconstituted fibrinogen solution tend to gelatinize if stored in the refrigerator for several days and cannot be used thereafter. At the same time, the fibrinogen is degraded fibrinogenolytically, which leads to a diminution of the clottable protein (Marder V J et al: High molecular weight derivatives of human fibrinogen produced by plasmin. I. Physicochemical and immunological characterization. J Biol Chem 1969; 244(8):2111-9).

In the past, different methods were used, such as chromatographic purification or other fractionation steps, which, though leading to better purified fibrinogen preparations, still had the disadvantages mentioned before (Kannelos J: Isolation of Fibrinogen by Affinity Chromatography. WO 97/26280; 1997. Hock J et al: Stable Fibrinogen Solution. U.S. Pat. No. 6,277,961 B1; 2001. Metzner H: Reinigung von Fibrinogen. EP 1 568 709 A2; 2005. Dazey B: Verfahren zur Herstellung von hochreinem Fibrinogen. DE 693 03 941 T2; 1993. Burnouf T: Chromatographische Trennung von Plasmaproteinen, insbesondere von Faktor VIII, von Willebrand Faktor, von Fibronektin and von Fibrinogen. DE 689 22 358 T3; 1990. Nogre M: Process for separating proteins fibrinogen, facor XIII and biological glue from a solubilized plasma fraction and for preparig lyophilised concentrates of said proteins. AU 2006202680 AT; 2005).

Attempts to achieve a longer storage stability and shorter reconstitution time of freeze-dried fibrinogen by increasing the salt concentration or by the addition of chaotropic agents have failed because of the required high osmolality and/or the occurrence of toxicity (Metzner H et al: Stabilized Protein Preparations for a Tissue Adhesive. U.S. Pat. No. 6,447,774 B1; 2002. Chabbat J: Fluid Biological Glue. WO 91/19519; 1991. Metzner H et al: Stabilisierte Proteinzubereitung für einen Gewebekleber. DE 198 53 033 A1; 2000).

Highly purified fibrinogen preparations which contain practically only clottable protein may consist of only half their functionally intact fibrinogen, particularly if stored over a prolonged period of time. The share of the non-intact fibrinogen in clottable protein consists of profibrin, fibrin monomers, and fibrin monomer complexes as well as still coagulable fibrinogen split products.

During the manufacture and storage of fibrinogen preparations, further fibrinogen split products may form to a varying degree by enzymatic action at the cost of functionally intact fibrinogen, leading to an impairment of the quality of a fibrinogen preparation, and in particular, to an impairment of the reconstitution of freeze-dried fibrinogen.

OBJECTIVE OF THE INVENTION

Freeze-dried, fibrinogen-containing medicinal products should be reconstitutable rapidly, this is within a short period of time, and should maintain this rapid reconstitutability for their whole shelf life. The fibrinogen solutions obtained by reconstitution with appropriate solvents should be storable at refrigerator temperature in liquid form and without major increase in viscosity for one week without losing clottable protein.

The clottable protein present in source materials already is a mixture of intact fibrinogen, profibrin, fibrin monomers, fibrin monomer complexes and also fibrinogenolytic split products. The split or degradation products of intact fibrinogen are formed by enzymes present in plasma and in plasma fractions mostly to varying degrees. Therefore, it is necessary to develop manufacturing methods which inhibit interfering enzymatic activities during production and which provide for the removal, as far as possible, of degradation products of the intact fibrinogen, particularly fibrin monomers and fibrin monomer complexes, since these prevent freeze-dried fibrinogen from reconstituting rapidly. Investigations by the inventors have shown that the stability of fibrinogen may depend strongly upon its content of enzymes which recognize fibrinogen as their substrate.

In order to avoid major losses of intact fibrinogen during production, any enzymatic processes which lead to a change in intact fibrinogen need to be prevented. Such enzymatic processes are caused by enzymes which recognize fibrinogen as their substrate and which are already present and/or form during the manufacturing process from their zymogens. In particular, with processing steps performed at room temperature or elevated room temperature, such as S/D virus inactivation, care needs to be used to prevent both, the formation of such enzymes from zymogens and the action of these enzymes on fibrinogen. Another requirement is the stability of functionally intact fibrinogen in a medicinal product which, when applied, has a fibrinogen concentration of between 0.3 and 10%.

Liquid, fibrinogen-containing medicinal products should be storable like freeze-dried fibrinogen in the refrigerator for a period of 18-36 months. During that period, there should be no major increase in viscosity and no loss in functionally intact fibrinogen.

SOLUTION OF THE OBJECTIVE ACCORDING TO THE INVENTION

The fibrinogen according to the invention may be produced from an aqueous solution, which contains functionally intact fibrinogen and is contaminated with profibrin and/or fibrin monomers and/or fibrin monomer complexes and/or fibrin split products, by precipitation of the impurities with a non-denaturing precipitating agent at a temperature between $-4°$ C. and $+4°$ C. and a Calcium ion activity that does not exceed that of a 1,000 µM $CaCl_2$ solution and separation by means of filtration or centrifugation from the aqueous solution. The filtrate or centrifugate, respectively, contains the fibrinogen according to the invention in liquid form.

The term "non-denaturing precipitating agent" refers to a precipitating agent that does not denature fibrinogen.

An essential feature of the method according to the invention hence is the reduction of the Calcium ion activity. It has shown that there may be obtained a fibrinogen, which may be reconstituted rather rapidly after being freeze-dried. In the sense of the present description and the present patent claims, rapid reconstitutability is defined as a reconstitution time of the freeze-dried fibrinogen at room temperature of maximum 10 minutes, as below described more comprehensively. Freeze-dried and state-of-the-art fibrinogen concentrates, in contrast, have much longer reconstitution times of about 20 to 30 minutes.

As starting material, fibrinogen-containing plasma raw fractions have proven suitable, which can be manufactured at temperatures ranging between $-4°$ and $+4°$ C. In this temperature range, enzymes which recognize fibrinogen as their substrate are slightly effective. On an industrial scale, such fibrinogen-containing plasma raw fractions can be obtained by alcohol precipitation of plasma or cryosupernatant as Cohn Fraction I or by cold precipitation as cryoprecipitate. The fibrinogen-containing plasma raw fractions Cohn Fraction I and cryoprecipitate are easily soluble in Water for Injections, and such fibrinogen-containing solutions can be stored deep-frozen until further use.

In plasma that has been obtained using inappropriate care, particularly if stored over a longer period of time, fibrin monomers and fibrin monomer complexes are present to a larger degree. If cryoprecipitates are obtained from such plasma, a large portion of such fibrin monomers is precipitated, so that it appears appropriate to obtain only the fibrinogen still present in the cryosupernatant by alcohol precipitation for further purification.

A preferred embodiment of the method according to the invention is characterized by the fact that during precipitation the aqueous solution has an electric conductivity of ≤500 µS/cm, preferably at a temperature between $0°$ C. and $2°$ C. It has shown that impurities may be precipitated more easily and to a higher degree under these conditions, so that the fibrinogen according to the invention is even more purified.

It is further preferred that the Calcium ion activity does not exceed that of a 500 µM $CaCl_2$ solution, especially not that of a 50 µM $CaCl_2$ solution.

Especially preferred is a variant of the method according to the invention, wherein the solution has a temperature between $0°$ and $2°$ C., an electric conductivity between 10 to 100 µS/cm and a Calcium ion activity that does not exceed that of a 500 µM $CaCl_2$ solution.

The fibrinogen that is contained in the obtained fibrinogen solution may be further purified by at least one further precipitation step.

In the method according to the invention, there may be produced a fibrinogen solution containing 0.3 to 10% clottable protein, which may be stored for up to 36 months at a temperature of $2°$ to $8°$ C., by removal of enzymes and their pro-enzymes, which as such or in their activated state recognize fibrinogen as substrate, with the help of non-denaturing precipitating means and, if necessary, by addition of corresponding virus inactivated, homologous protease inhibitors.

The fibrinogen solution will preferably be subjected a procedure for virus inactivation or virus removal or depletion, which is carried out at temperatures above room temperature, a thrombin activity of ≤0.3 IE/ml and a Calcium ion activity that does not exceed that of a 1,000 µM $CaCl_2$ solution.

The viruses may be removed by nanofiltration at temperatures between $20°$ and $40°$ C. and with nanofilters having a pore size of maximum 20 nm, preferably 15 nm, wherein nanofiltration is preferably carried out so that this does not result in splitting off fibrinopeptide A.

The fibrinogen solution produced according to the invention is usefully concentrated, deep-frozen or freeze-dried.

The invention further relates to a fibrinogen concentrate, which may be obtained through the method according to the invention.

The fibrinogen concentrate in its freeze-dried form is further preferred, for use as a pharmaceutical drug substance, wherein the concentrate can be reconstituted with a suitable solvent to a 0.3% to 10% fibrinogen solution, and may be stored for at least 10 days between $2°$ and $8°$ C., without the content of clottable protein decreasing or a gel being formed.

The freeze-dried fibrinogen concentrate may be reconstituted after a storage time of at least 18 months at $2°$ to $8°$ C. with a solvent within less than 10 minutes.

A preferred embodiment of the fibrinogen concentrate according to the invention contains fibrinogen, from which there may be split off with thrombin at least 70% fibrinopeptide A, based on the clottable protein.

Further preferred embodiments of the fibrinogen concentrate according to the invention are characterized in that
    they contain at least 1 arbitrary unit AT-I per 10 mg clottable protein, or
    they contain no particles with a diameter of more than 20 nm, preferably 15 nm, or
    they were heated after freeze-drying for 30 to 180 minutes to a temperature of $90°$ to $145°$ C.

Furthermore, the invention relates to a medicinal product containing the fibrinogen concentrate according to the invention as an active substance.

The medicinal product according to the invention may be contained in a pre-filled syringe or in an infusion bag.

The invention further relates to a method for producing a medicinal product, which contains the freeze-dried fibrinogen concentrate and to which there have been added basic amino acids up to the half of the weight of the clottable protein, as well as salts in order to guarantee for osmolarity, wherein the freeze-dried fibrinogen concentrate is reconstituted in a solvent containing an amount of Ca salt, which guarantees that the reconstituted product has a Calcium ion activity corresponding to that of 5 mM Ca—Cl$_2$ solution.

The medicinal product according to the invention in freeze-dried form may furthermore be heat-treated in a final container for a period of time of 30 to 100 minutes at temperatures between 90° and 145° C. for inactivating possibly present viruses.

Finally, the invention relates to the use of the fibrinogen solution according to the invention or of the fibrinogen concentrate according to the invention for producing a medicinal product for the treatment of a-, dys- and hypofinbrinogenemia and for the treatment of patients with consumption coagulopathy and shock, especially septic shock.

The invention will be further described in the following.

As already mentioned above, for the manufacture of fibrinogen concentrates with a high content of functionally intact fibrinogen it is necessary to inhibit the action of enzymes which recognize fibrinogen as their substrate as much as possible, equally so the formation of such enzymes from their zymogens. According to the invention, this is achieved by a strong reduction of the calcium ion activity and the strict observance of a temperature range between 2° and 4° C. By the addition of EDTA, the calcium ion activity is lowered to the extent that it lies below the ion activity of a 1,000 μM CaCl2 solution. By fractionated precipitation with the aid of non-denaturing fibrinogen precipitating agents, e.g. glycine, a fribrinogen fraction of at least 90% clottable protein can be obtained. If necessary, a fibrinogen concentrate can be obtained by multiple reprecipitation, from which, based on clottable protein, at least 70% Fibrinopeptide A can be split off by thrombin and which can be reconstituted promptly after freeze-drying. If such fibrinogen concentrates contain too high thrombin or kallikrein activity in a 1% solution, the reduction in enzyme activity is reached by the addition of enzyme-free inhibitors. It is appropriate to add virally safe inhibitors, which can, if necessary, be removed again by further purification steps.

Virus inactivation can, therefore, be performed by the addition of Tween-80 and trinitrobutylphsphate in the required amounts at temperatures ranging from 28° to 30° C. for up to ten hours, without measurable amounts of Fibrinogenpeptide A being split from fibrinogen.

The virus inactivating agent can be removed from virus inactivated fibrinogen raw concentrate chromatographically or by fractionated precipitation. Amino acids, polyethylen glycol and other, non-toxic and non-denaturing precipitating agents can be used for precipitation at temperatures above 0° C. In addition, there is the possibility to remove Tween 80 and trinitrobutylphosphate by alcohol fractionation at temperatures between −3° and −5° C.

The virus inactivated and purified fibrinogen concentrate still may contain fibrin monomers and fibrin monomer complexes, which can be removed by cold precipitation at very low electric conductivity. Lowering the conductivity to below 500 μS/cm and in particular between 10 and 100 μS/cm can be achieved by dialysis, diafiltration or alcohol precipitation in the cold.

Cold precipitation is performed at temperatures between −4° and +4° C. and a pH ranging from 7.1 to 7.3. Lowering the pH to 6.5 increases the cold precipitation, however, diminishes the yield of functionally intact fibrinogen. Stirring, vibration or supersonic sounding increase the cold precipitation. The cold precipitate, which essentially consists of fibrin monomers and their complexes, is removed by filtration or centrifugation. The supernatant or filtrate contain the functionally intact fibrinogen, which can be obtained by precipitation, preferably with alcohol below 0° C. The fibrinogen, highly purified in that manner, is functionally intact and can be reconstituted promptly after freeze-drying. During the whole manufacturing process, care needs to be taken that the calcium ion activity does not exceed that of a 1,000 μM CaCl$_2$ solution.

If necessary, proenzymes such as factor XIII or plasminogen can be removed by further purification steps. However, certain proenzymes are necessary for some applications. They are preferably added in virus inactivated form during formulation of a fibrinogen preparation.

The highly purified fibrinogen concentrate may still contain enzymes, albeit in low concentration, which adversely affect fibrinogen. In order to inhibit these enzymes, virus inactivated, atoxic, enzyme-free, homologous protease inhibitors are added, such as AT-III, heparin cofactor II, and C$_1$ esterase inhibitor. The fibrinogen concentrates obtained in that manner, having preferably a calcium ion activity below that of a 50 μM CaCl$_2$ solution, can be stored for at least 18 months in liquid state as a drug substance or formulated in a concentration range of fibrinogen between 0.3 and 10% at 2° to 8° C. Fibrinogen solutions which no longer have thrombin activity may still contain thrombin which is bound to sites of the fibrinogen molecule which cannot be split off by thrombin. By the addition of non-toxic chaotropic substances, the fibrinogen-thrombin bond may be disrupted, and thrombin may be separated from fibrinogen. The fibrinogen purified in that manner has a high AT-I activity. The chaotropic substances are removed again by reprecipitation.

The potential risk of virus transmission by human blood products can be reduced by nanofiltration. Fibrinogen solutions which contain no or only small amounts of fibrin monomer complexes can be filtered easily through nanofilters having a pore size of 15 to 20 nm, an increase in the temperature of the solution to be filtered above room temperature accelerating the filtration rate. Practically enzyme-free fibrinogen solutions can be nanofiltered up to a temperature of 40° C., and in that manner, one can achieve at least double an increase in the filtration rate.

Another reduction in the risk of virus transmission is achieved by heating of freeze-dried fibrinogen to temperatures of between 90° and 145° C. for a period of 30 to 180 minutes. This heating may be performed either on freeze-dried bulk material or in final containers.

According to the invention, the improvements in the production of fibrinogen render possible the manufacture of fibrinogen-containing medicinal products which can be stored and transported more easily, and which render possible a more rapid and wider therapeutic application.

The invention, therefore, concerns a freeze-dried fibrinogen concentrate as a pharmaceutical drug substance which, when reconstituted with an appropriate solvent to a 0.3 to 10% fibrinogen solution, can be stored for at least 10 days at a temperature ranging from 2° to 8° C., without a loss in clottable protein or without gel formation.

A preferred embodiment of the freeze-dried fibrinogen concentrate according to the invention is characterized in that it can be reconstituted rapidly with solvents during a storage period of 18 months at 2° to 8° C.

A further embodiment of the fibrinogen concentrate according to the invention is characterized in that its content of clottable protein consists of functionally intact fibrinogen and less than 10%, preferably less than 3%, profibrin and/or fibrin monomers, is virus inactivated, and if stored in freeze-dried form at temperatures ranging from 2° to 8° C., is spontaneously soluble in quantities of solvents yielding 0.3 to 10% solutions of clottable protein, these solutions when stored over up to ten days at 2° to 8° C. not being subject to change in viscosity or a decrease in clottable protein.

A further embodiment of the fibrinogen concentrate according to the invention is characterized in that it contains neither enzymes which recognize fibrinogen as a substrate nor proenzymes which can be activated into such enzymes and that it is storable in a 0.3 to 10% solution at 2° to 8° C. for at least 18, preferably 36 months.

Furthermore, the invention concerns processes for the manufacture of fibrinogen concentrates having an AT-I activity of at least one arbitrary unit of AT-I per 10 mg clottable protein by fractionated precipitation with non-denaturing precipitating agents, after prior disruption of the enzyme-substrate-bond of thrombin with fibrinogen by non-toxic chaotropic substances, The following examples illustrate the preferred embodiments of the invention in greater detail:

EXAMPLES

1. Promptly Reconstitutable, Freeze-Dried Fibrinogen Concentrate 1000 g of cryopaste or Cohn Fraction I precipitate are dissolved in a 0.01 M EDTA solution which contains 2 Upper ml under constant stirring at 4°±1° C., in order to obtain a 1-2% protein solution Anhydrous glycine is added to this solution under stirring until the content is 6 g/v %. After 10 hours of stirring at 2° C., the resulting precipitate is removed in a temperature range of 2°-4° C. by centrifugation or filtration. The precipitate contains a large part of the fibrin monomer complexes and fibrin monomers contained in the source material. The supernatant or the filtrate are saturated with glycine at a temperature of between 2° and 4° C. and are stirred again for 10 hours at this temperature. The precipitated fibrinogen is obtained by high rotational speed in a Sharples centrifuge at a speed of approximately 17000 revolutions per minute and is dissolved again in a 1/100 M EDTA solution to obtain an approximately 1% solution of clottable protein.

The dissolved fibrinogen is kept at a temperature of 2° to 4° C., and a sample is taken for the determination of thrombin, total protein, and clottable protein.

The calcium ion activity of the solution, in which impurities have been precipitated, was below that of 500 µM $CaCl_2$ solution. The calcium ion activity was determined using a calcium electrode, and the value of the ion activity was evaluated on the basis of a curve representing the dependency of the voltage measured by the electrode on the $CaCl_2$ concentration. If the calcium ion concentration is too high, the calcium ion activity is correspondingly lowered by means of a 1/10 M EDTA solution.

The thrombin activity must not amount to more than 1 mU of thrombin per ml. Determination of thrombin is performed with chromogenic substrate 2238 with respect to a thrombin reference preparation. If the thrombin content is more than 1 mU of thrombin per ml, the thrombin activity is inhibited by the addition of AT-III and heparin in a unit ratio of 1+3 or by reprecipitation with glycine.

If necessary, glycine can be removed largely from the fibrinogen solution by diafiltration, equally so by reprecipitation with alcohol below 0° C. For storage until further use, the fibrinogen solution can be kept frozen at −20° C. or be manufactured into fibrinogen storable at 4° C. by freeze-drying, which is promptly soluble.

2. Virus Inactivated, Promptly Soluble Fibrinogen Concentrate

The approximately 1% protein solution of the fibrinogen concentrate prepared according to Example 1 is admixed with the required amount of Tween 80 and trinitrobutylphosphate and kept at 30° C. for 10 hours. A virus inactivation test performed before that ensures that storage of a sample for a period of 30 hours will not cause fibropeptide A to be released. In order to remove the added Tween 80 and trinitrobutylphosphate, reprecipitations are performed with non-denaturing precipitating agents, such as glycine or alcohol below 0° C. up to an alcohol content of 10%.

Virus inactivated fibrinogen concentrate can be stored either deep-frozen or freeze-dried and can be thawed and promptly reconstituted, respectively, thereafter.

3. Functionally Intact, Virus Inactivated Fibrinogen Promptly Soluble 10 liters of a solution produced according to Example 2 with 1% virus inactivated, clottable protein are adjusted to an electric conductivity of 10 to 100 µS by diafiltration against a 1/100 M EDTA solution or by reprecipitation with ethyl alcohol and dissolution of the alcohol precipitate in a 1/100 M EDTA solution. The pH of the solution is adjusted to between 7.1 and 7.3, and the solution is kept at a temperature of between 2° and 4° C. for 10 hours under slight stirring. This causes the fibrin monomer complexes still present in the solution to precipitate and also causes a partial precipitation of fibrin monomers. By centrifugation at approximately 17000 revolutions per minute in a Sharples centrifuge, the precipitate is separated. If the supernatant is still opalescent, filtration is performed using a filter with 5 µL. The solution obtained in that manner has a content of at least 90% functionally intact fibrinogen in reference to the clottable protein present in the solution. By lowering the pH to 6.5, the percent content of functionally intact fibrinogen can be increased even further, which, however, entails a loss in yield. The solutions of functionally intact fibrinogen obtained in that manner can be stored deep-frozen or freeze-dried in bulk until further processing or until their formulation into medicinal products.

4. Functionally Intact Fibrinogen, Virus Inactivated, Storable in Liquid Form

Solutions of functionally intact fibrinogen as these are obtained according to Example 3 may still contain enzymes which change fibrinogen enzymatically. Therefore, it is necessary to inhibit such enzyme activities by atoxic, virus inactivated enzyme inhibitors obtained from human plasma. For that purpose, the thrombin and kallikrein activities are determined in the fibrinogen concentrate, and virus inactivated and enzyme-free AT-III is added until thrombin activity cannot be detected any longer. Heparin is not added. In order to inhibit the kallikrein activity, a $C_1$-esterase inhibitor from human plasma needs to be added which contains no enzymatic activities and is virally safe. Chromogenic substrate 2302 is used for the determination of kallikrein activity.

Enzyme-free solutions of functionally intact fibrinogen are manufactured in concentrations of 0.3 to 10% by diafiltration or precipitation with alcohol and dissolution of the alcohol precipitate and are storable at temperatures between 2° and 8° C.

5. Manufacture of Functionally Intact, Virus Inactivated Fibrinogen Concentrate with a High AT-I Content The enzyme-free fibrinogen concentrate manufactured according to Example 4 contains further thrombin bound to fibrinogen at sites of the molecule which are not split enzymatically by thrombin. In order to disrupt the bond between fibrinogen and thrombin, 2 g of urea are added to the solution per g of intact fibrinogen, and the mixture is stirred slightly for one hour at 35° C. Thereafter, fibrinogen is precipitated with sodium citrate in a pH range of between 7.4 and 7.8, the precipitate is obtained by centrifugation and, if necessary, is reprecipitated one or several times with sodium citrate, the dissolved precipitate containing 2 g urea per g fibrinogen. At the end, the fibrinogen solution is diafiltered against a 1/100 M EDTA solution to remove the urea and the citrate. The diafiltered solution is storable at temperatures between 2° and 8°. The solution can also be manufactured into freeze-dried fibrinogen.

6. Nanofiltered Fibrinogen Concentrate

The fibrinogen concentrates manufactured according to Examples 2 to 5 can also be nanofiltered to increase virus safety, preferably in a fibrinogen concentration of between 0.1 and 1%. Prior to nanofiltration, the fibrinogen-containing solutions are clarified by filtration using filters of 75 nm to 35 nm, followed by nanofiltration through nanofilters with a pore size of 20 nm or 15 nm. To the extent that the fibrinogen concentrations have no enzymatic activity, nanofiltration can be performed at temperatures of up to 40° C. to increase the filtration rate.

7. Heat Treatment of Freeze-Dried, Spontaneously Soluble, Functionally Intact, Virus Inactivated Fibrinogen Freeze-dried fibrinogen concentrate is pulverized and passed through a sieve with a mesh opening of 0.5 mm. The fibrinogen powder is brought to a moisture content of 0.8 to 1% and then exposed to a strong air stream at a temperature of 100° C. for 30 minutes in a closed container. After cooling to room temperature, the heated fibrinogen powder is closed moisture tight and stored at a temperature of 2° to 8° C.

8. Determination of the Reconstitution Time of Freeze-Dried Fibrinogen

The term "reconstitution time" refers, in the sense of the present description and the patent claims, to that period of time extending from the point of addition of a solvent to the freeze-dried fibrinogen to its complete dissolution, wherein the freeze-dried fibrinogen is only then considered as dissolved when at least 97% are dissolved and not more than 3% remain not dissolved.

The reconstitution time is now determined as follows:

Portions of 500 mg fibrinogen are weighed—on the basis of clottable protein—in 6 centrifuge vessels each, which are then mixed with 10 ml 0.9% saline each and then shaken on a Biodancer (New Brunswick Scientific Edison, N.J., USA) at "Speed 2.0" and at room temperature.

After 3, 5, 10, 15, 20 and 30 minutes, there is removed one centrifuge glass and centrifugated for 10 minutes, wherein the system is adjusted to 10,000 rpm. The sediments contained in the 6 centrifuge glasses are washed with 0.9% saline three times, and the protein content of the sediments is determined after the third washing. In order to determine the protein, there is used the Bradford reagent by Biorad. The protein content is evaluated according to a reference curve, which has been elaborated by means of the Biorad reagent and fibrinogen. The reconstitution time in minutes is now that period of time after the addition of the solvent, at which there are present less than 3% of the clottable protein in a not-dissolved state.

A rapid reconstitution time is provided then in the sense of the present description and the patent claims when there is required not more than 10 minutes, especially between 3 to 5 minutes, in order to produce 10 ml of 5% fibrinogen solution at room temperature by little shaking without foam formation.

The fibrinogen concentrates prepared according to the invention and freeze-dried have a reconstitution time of less than 10 minutes, especially between 3 to 5 minutes. In contrast thereto, the reconstitution time of two prior art fibrinogen concentrates was measured to be 20 minutes or more than 30 minutes, respectively.

The invention claimed is:

1. A method for producing a fibrinogen solution from an aqueous solution containing functionally intact fibrinogen and being contaminated with contaminants including profibrin and/or fibrin monomers and/or fibrin monomer complexes and/or fibrin split products, wherein the contaminants are precipitated with a non-denaturing precipitating agent at a temperature between −4° to +4° C. and a calcium ion activity not higher than that of a 1,000 µM $CaCl_2$-solution, and are separated by filtration or centrifugation from the aqueous solution.

2. A method according to claim 1, wherein the aqueous solution has a temperature between 0° and 2° C. and an electric conductivity of <500 µS/cm when it is precipitated.

3. A method according to claim 1, wherein the calcium ion activity is not exceeding that of a 500 µM $CaCl_2$ solution.

4. A method according to claim 3, wherein the calcium ion activity is not exceeding than that of a 50 µM $CaCl_2$ solution.

5. A method according to claim 2, wherein the solution has a temperature between 0° and 2° C., an electric conductivity between 10 to 100 µS/cm and a calcium ion activity not exceeding that of a 500 µM $CaCl_2$ solution.

6. A method according to claim 1, wherein the fibrinogen contained in the obtained fibrinogen solution is further purified by at least one more precipitation step.

7. A method according to claim 1, comprising obtaining a fibrinogen solution containing 0.3% to 10% clottable protein, which is storable up to 36 months at a temperature of 2° to 8° C., by removal of enzymes and their pro-enzymes which, as such or in activated form, recognize fibrinogen as a substrate, using non-denaturing precipitating agents and, optionally, by adding appropriate virus inactivated, homologous protease inhibitors.

8. A method according to claim 1, wherein the fibrinogen solution is subjected to a method for virus inactivation or virus removal, which is carried out at temperatures above room temperature, a thrombin activity of <0.03 IE/ml and a calcium ion activity not exceeding that of a 1,000 µM $CaCl_2$ solution.

9. A method according to claim 8, wherein the viruses are removed by means of nanofiltration at temperatures between 20° and 40° C. and using nanofilters with a pore size of at most 20 nm, said nanofiltration being carried out in a way so that fibrinopeptide A is not split off from fibrinogen.

10. A method for producing a fibrinogen concentrate, wherein a fibrinogen solution produced according to claim 1 is concentrated, deep-frozen or freeze-dried.

11. A method for the manufacture of a medicinal product containing a freeze-dried fibrinogen concentrate according to claim 10 and to which basic amino acids up to half of the weight of clottable protein are added, as well as salts, in order to provide osmolality, the freeze-dried fibrinogen concentrates being reconstituted in a solvent containing an amount of calcium salt ensuring that the reconstituted product has a calcium ion activity corresponding to that of a 5 mM $CaCl_2$ solution.

12. A method according to claim 10, comprising heat inactivation of viruses in final containers for a period of 30 to 100 minutes at temperatures between 90° and 145° C.

13. A method according to claim 1, wherein the calcium ion activity of the aqueous solution is lowered by adding EDTA and that glycine is used as non-denaturing precipitating agent.

14. A method according to claim 2, wherein reduction of electric conductivity of the aqueous solution is realized by dialysis, diafiltration or alcohol precipitation in the cold.

* * * * *